United States Patent [19]
Wilk

[11] Patent Number: 6,155,968
[45] Date of Patent: Dec. 5, 2000

[54] METHOD AND DEVICE FOR IMPROVING CARDIAC FUNCTION

[76] Inventor: Peter J. Wilk, 185 West End Ave., New York, N.Y. 10023

[21] Appl. No.: 09/121,477

[22] Filed: Jul. 23, 1998

[51] Int. Cl.⁷ ....................................................... A61F 1/00
[52] U.S. Cl. ................................. 600/16; 600/37; 128/898
[58] Field of Search ............................... 601/153; 600/16, 600/37; 606/153, 157, 158, 151, 139; 128/898, 899

[56] References Cited

U.S. PATENT DOCUMENTS

| | | | |
|---|---|---|---|
| 5,766,216 | 6/1998 | Gangal et al. | 606/140 |
| 5,800,528 | 9/1998 | Lederman et al. | 623/3 |
| 5,865,791 | 2/1999 | Whayne et al. | 604/49 |
| 5,928,250 | 7/1999 | Koike et al. | 606/139 |
| 5,961,440 | 10/1999 | Schweich et al. | 600/16 |

*Primary Examiner*—Cary O'Connor
*Attorney, Agent, or Firm*—R. Neil Sudol; Henry D. Coleman; William J. Sapone

[57] ABSTRACT

In a method for improving cardiac function, a compressive device is inserted into an intrapericardial space about a lower end portion of a heart. Thereafter the compressive device is operated to compress and close off lower portions of both ventricles of the heart.

12 Claims, 2 Drawing Sheets

METHOD AND DEVICE FOR IMPROVING CARDIAC FUNCTION

BACKGROUND OF THE INVENTION

This invention relates to a method and device for improving cardiac function, particularly where there is congestive heart failure.

Congestive heart failure occurs, inter alia, where there has been a heart attack or an infection. In either case, the pumping action of the heart is impaired. In another malfunction, left ventricular hypertrophy, the myocardium of the left ventricle becomes thickened to the point of interfering with effective heart contraction.

A surgical procedure for treating congestive heart failure, developed by a doctor in Brazil, involves removing a triangular portion of a patient's heart. In this operation, approximately one-third of the patient's left ventricular muscle is removed. The result is that the smaller heart pumps more efficiently.

This new technique of course requires open heart surgery, with its attendant expense and extended convalescence.

OBJECTS OF THE INVENTION

An object of the present invention is to provide a surgical method for treating congestive heart failure.

A further object of the present invention is to provide such a surgical method which is less expensive than the above-described surgical technique.

It is another object of the present invention to provide a surgical method for treating congestive heart failure which may be implemented through minimally invasive procedures.

An additional objet of the present invention is to provide a device for implementing such a surgical method.

These and other objects of the present invention will be apparent from the drawings and descriptions herein.

SUMMARY OF THE INVENTION

A method for improving cardiac function comprises, in accordance with the present invention, inserting a compressive device into an intrapericardial space about a lower end portion of a heart, and thereafter operating the compressive device to compress and close off lower portions of both ventricles of the heart.

Wherein the compressive device includes a plurality of prongs or tines each connected at one end to the other prongs or tines, the operating of the compressive device includes pivoting each of the prongs or tines about the respective one end.

At least one of the prongs or tines, and preferably a plurality thereof, is provided with a tooth which is inserted into the heart muscle. The tooth ensures an adequate grip of the compressive device on the heart muscle, thereby preventing slippage.

The operating of the compressive device may include actuating a camming mechanism to pivot each of the prongs or tines about the respective one end. The camming mechanism functions to move the prongs or tines in a radial direction in response to an axial movement of a tubular member about the prongs or tines. An elastic ring or collar may be simply pushed down over the prongs or tines and locked thereto, for example, by a snap-lock catch or detent.

Although the present invention may be performed in an open-heart procedure, it is preferred that the compressive device be inserted in a minimally invasive operation, i.e., through a trocar sleeve or cannula.

In a modified configuration, the compressive device includes a plurality of overlapping leaves, the leaves being provided with gaps for receiving coronary arteries during a closure of the compressive device about the lower end portion of the heart. The inserting of the compressive device then includes aligning the gaps with respective ones of the coronary arteries.

A device for improving cardiac function comprises, in accordance with the present invention, a plurality of prongs or tines each connected at one end to the other prongs or tines, and a closure mechanism operative connected to the prongs or tines for pivoting each of the prongs or tines about the respective one end thereof.

A surgical method in accordance with the present invention treats congestive heart failure. The method may be performed thoracoscopically which is less expensive and less traumatic to the patient than an open-heart surgical technique. The method of the invention is simple and reliable.

DESCRIPTION OF THE PREFERRED EMBODIMENTS

Figure 1:
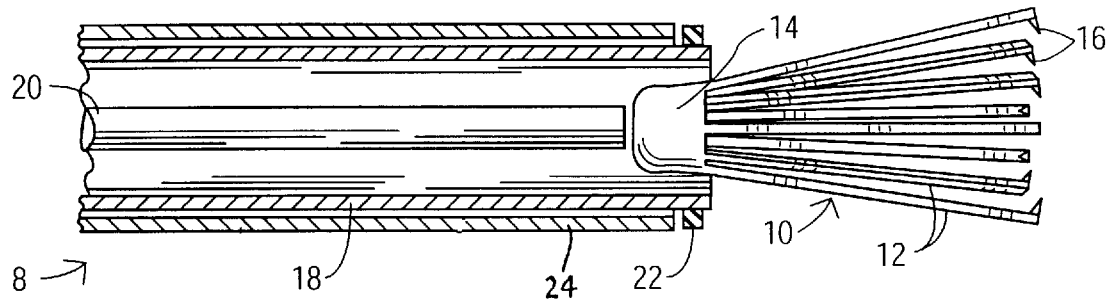
FIG. 1 is a schematic partial longitudinal cross-sectional view of an instrument or device for operating on the heart to improve cardiac function.
Figure 2A:
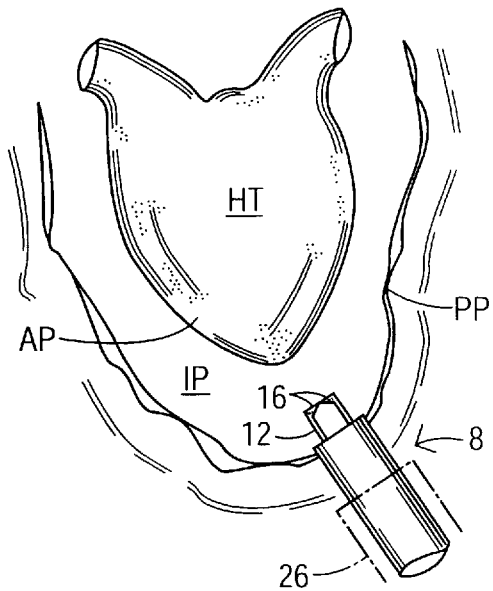
FIGS. 2A–2D are schematic views of a person's heart, showing successive steps in a surgical procedure for improving cardiac function, in accordance with the present invention.
Figure 2B:
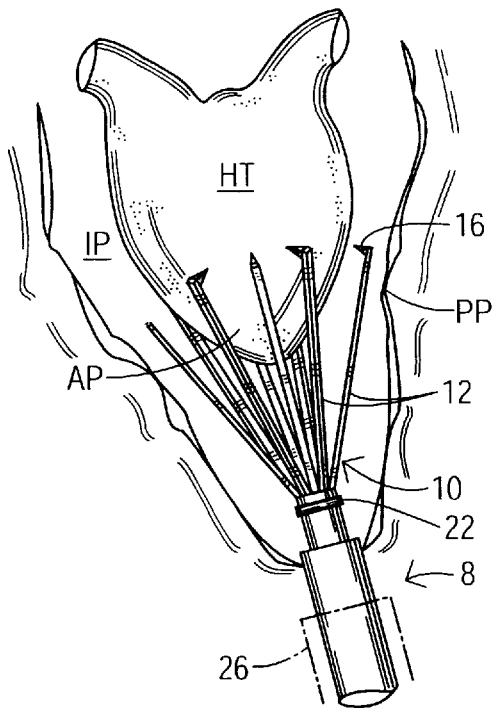

FIG. 1 illustrates a medical device 8 for use in performing surgery as discussed below with reference to FIGS. 2A through 2D to improve cardiac function by reducing the effective volume of the ventricles. The device includes a cardiac clamp 10 in the form of a plurality of elongate prongs or tines 12 connected in a substantially circular or oval configuration to a base 14. Prongs 12 have an inherent spring bias which tends to spread the prongs into a conical configuration as depicted in FIGS. 1 and 2B. Prongs 12 are each provided with at least one tooth 16 which faces inwardly relative to the spread-open conical configuration.

Device 8 further includes an inner tubular member 18 in which clamp 10 is disposed in a collapsed configuration at the onset of a surgical procedure. More specifically, clamp 10 is disposed inside a distal end portion of tubular member 18 prior to an ejection of the clamp by a distally directed motion of a rod 20. Prior to use, rod 20 may be disposed outside of tubular member 18. It is preferable, however, that rod be disposed partially inside tubular member 18 during initial deployment thereof during a cardiac operation as discussed below.

An elastic band 22 is disposed about tubular member 18 at the distal end thereof. A second tubular member 24 surrounds tubular member 18 for pushing band 22 off of the distal end of tubular member 18 as discussed below.

As illustrated in FIG. 1, a distal end portion of tubular member 18 is inserted through parietal pericardium PP into an intrapericardial space IP surrounding a patient's heart HT. Tubular member 18 may be deployed in an open heart surgical operation or alternatively in a minimally invasive operation. In the latter case, tubular member is inserted through a thoracoscopic cannula or trocar sleeve 26.

Figure 2C:
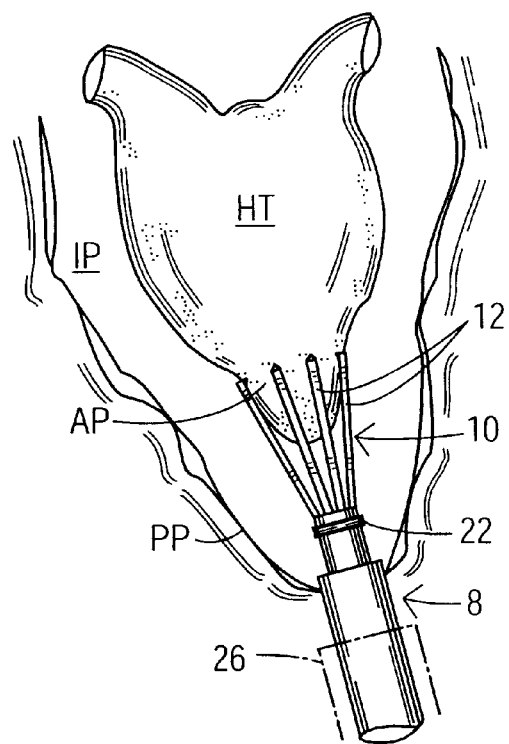

Tubular member 18 is inserted from below the heart HT so that the distal end is pointed upwardly substantially parallel to the septum (not shown). After a proper positioning of tubular member 18, rod 20 is pushed in the distal direction, towards an apical portion AP of the heart HT to eject clamp 10, as shown in FIG. 2A. Upon the ejection of clamp 10, prongs 12 automatically spread open under their inherent spring bias to form a conical configuration. The entire instrument assembly is then moved towards heart HT so that the opened clamp 10 surrounds apical portion AP, as illustrated in FIG. 2B. Subsequently, inner tubular member 18 is pushed forward, over clamp 10, as depicted in FIG. 2C. Prongs 12 are pressed inwardly in a camming type action so that teeth 16 bite into the myocardium of heart HT and anchor clamp 10 thereto. Continued forward or distal motion of inner tubular member 18 relative to clamp 10 serves to compress apical portion AP of heart HT, as shown in FIG. 2C. To some extent, prongs 12 pivot about the connecting points to base 14 in response to the camming action of tubular member 18.

Figure 2D:
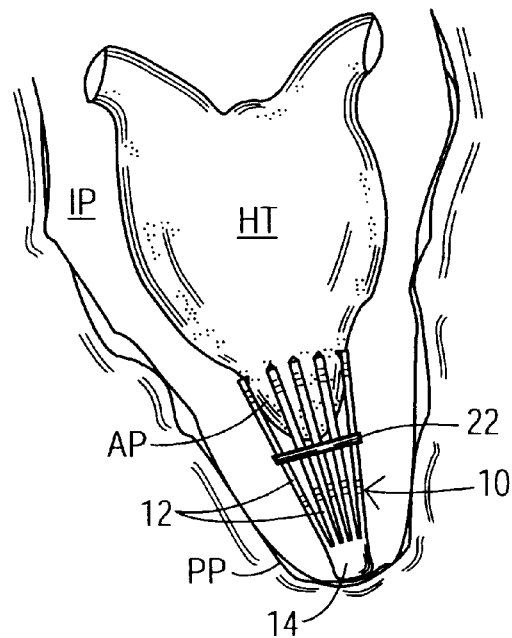

After the positioning and partial closure of clamp 10 about the apical portion AP of heart HT, outer tubular member 24 is shifted in the distal direction toward heart, while clamp 10 and inner tubular member 18 are maintained in position about apical heart portion AP. This relative motion serves to slide or push elastic band 22 off of tubular member 18 and onto the closed clamp 10. As illustrated in FIG. 2D, band 22 is left in place on clamp 10 to hold prongs 12 in a partially closed configuration compressing apical portion AP of heart HT and reducing the volume of both ventricles of the heart. The reduced volume makes the pumping action of the heart more efficient and improves blood circulation in individuals suffering from congestive heart failure or left ventricular hypertrophy.

Although the invention has been described in terms of particular embodiments and applications, one of ordinary skill in the art, in light of this teaching, can generate additional embodiments and modifications without departing from the spirit of or exceeding the scope of the claimed invention. For example, other mechanisms for closing a compressive device about a lower end of a patient's heart will be apparent to those skilled in the art. Such mechanisms will generally contemplate the conversion of an axially directed force to a compressive force. In one alternative design, instead of pushing tubular member 18 about the expanded clamp 10, a screw mechanism may be used to close, and possibly open, prongs 12. In another alternative design, a cup-shaped clamp has a plurality of relative movable leaves, as in a mechanical iris.

It is to be noted, in addition, that device 8 may be used to place clamp 10 about a part of the heart HT other than apical portion AP. Thus, device 8 may approach the heart HT from a different direction, for example, where it is desired to reduce the effective volume of the left ventricle only.

Prongs 12 may be spring biased to close clamp 10. In that case, the inserting instrument is adapted to spread prongs 12 into a opened configuration in opposition to the action of inherent spring forces. When the opening force is removed, the clamp squeezes the hear muscle and compresses a portion of the heart.

A catch may be provided on prongs 12 for holding band 22 on clamp 10 after the disposition of band about the clamp.

Accordingly, it is to be understood that the drawings and descriptions herein are preferred by way of example to facilitate comprehension of the invention and should not be construed to limit the scope thereof.

What is claimed is:

1. A method for improving cardiac function, comprising:
    inserting a compressive device into an intrapericardial space about a lower end portion of a heart; and
    after the inserting of said compressive device into the intrapericardial space, operating said compressive device to compress and close off lower portions of both ventricles of the heart.

2. The method defined in claim 1 wherein said compressive device includes a plurality of prongs or tines each connected at one end to the other prongs or tines, the operating of said compressive device including pivoting each of said prongs or tines about the respective one end.

3. The method defined in claim 2 wherein at least one of said prongs or tines is provided with a tooth, further comprising inserting said tooth into the heart.

4. The method defined in claim 2 wherein the operating of said compressive device includes turning a camming mechanism to pivot each of said prongs or tines about the respective one end.

5. The method defined in claim 2 wherein the inserting of said compressive device includes inserting said compressive device through a trocar sleeve or cannula.

6. The method defined in claim 1 wherein the inserting of said compressive device includes inserting said compressive device through a trocar sleeve or cannula.

7. A method for improving cardiac function, comprising:
    inserting a compressive device having a plurality of spaced members into an intrapericardial space about a portion of a heart, at least one of said spaced members being provided with a tooth;
    after the inserting of said compressive device into the intrapericardial space, operating said compressive device to compress and close off a portion of at least one ventricle of the heart; and
    inserting said tooth into the heart to anchor said compressive device to the heart.

8. The method defined in claim 7 wherein said spaced members are a plurality of prongs or tines each connected at one end to the other prongs or tines, the operating of said compressive device including pivoting each of said prongs or tines about the respective one end.

9. The method defined in claim 8 wherein the operating of said compressive device includes turning a camming mechanism to pivot each of said prongs or tines about the respective one end.

10. The method defined in claim 7 wherein said spaced members are provided with a plurality of teeth, further comprising inserting said teeth into the heart to anchor said compressive device to the heart.

11. The method defined in claim 7 wherein the inserting of said compressive device includes inserting said compressive device through a trocar sleeve or cannula.

12. A method for improving cardiac function, comprising:
    inserting a compressive device into an intrapericardial space about a lower end portion of a heart, said compressive device including a plurality of prongs or tines each connected at one end to the other prongs or tines; and
    after the inserting of said compressive device into the intrapericardial space, operating said compressive device to compress and close off lower portions of both ventricles of the heart, the operating of said compressive device including pivoting each of said prongs or tines about the respective one end, the operating of said compressive device further including turning a camming mechanism to pivot each of said prongs or tines about the respective one end.

* * * * *